(12) United States Patent
Liu et al.

(10) Patent No.: US 9,315,874 B2
(45) Date of Patent: Apr. 19, 2016

(54) BACILLUS SUBTILIS MUTANT STRAIN AND A FERMENTATION METHOD FOR PRODUCING ACETOIN USING THIS ORGANISM

(75) Inventors: Jianjun Liu, Jinan (CN); Xiangying Zhao, Jinan (CN); Jiaxiang Zhang, Jinan (CN); Yanjun Tian, Jinan (CN); Yanlei Han, Jinan (CN); Li Han, Jinan (CN)

(73) Assignee: Shandong Food Fermentation Industry Research & Design Institute, Jinan (CN)

( * ) Notice: Subject to any disclaimer, the term of this patent is extended or adjusted under 35 U.S.C. 154(b) by 1105 days.

(21) Appl. No.: 11/970,573

(22) Filed: Jan. 8, 2008

(65) Prior Publication Data

US 2008/0182306 A1 Jul. 31, 2008

(30) Foreign Application Priority Data

Jan. 29, 2007 (CN) .......................... 2007 1 0013402
Jan. 29, 2007 (CN) .......................... 2007 1 0013403

(51) Int. Cl.
*C12N 1/20* (2006.01)
*C12R 1/125* (2006.01)
*C12P 7/26* (2006.01)

(52) U.S. Cl.
CPC .. *C12R 1/125* (2013.01); *C12P 7/26* (2013.01)

(58) Field of Classification Search
None
See application file for complete search history.

(56) References Cited

U.S. PATENT DOCUMENTS

2009/0215152 A1* 8/2009 Xu et al. .................... 435/252.5

OTHER PUBLICATIONS

Lopez et al., Eur. J. Biochem. 40,479-483 (1973).*
Xiao et al., Appl Microbiol Biotechnol (2007) 74:61-68.*
http://www.atcc.org/ATCCAdvancedCatalogSearch/tabid/112/Default.aspx, accessed Jan. 24, 2011.*
Yoshida et al., Journal of Bacteriology, Feb. 2002, p. 983-991 vol. 184, No. 4.*
Morinaga et al., Bioscience, Biotechnology, and Biochemistry, vol. 70 (2006), No. 8 pp. 1913-1920.*

* cited by examiner

*Primary Examiner* — Irene Marx
(74) *Attorney, Agent, or Firm* — Oliff PLC

(57) ABSTRACT

The present invention provides a mutant strain of *Bacillus subtilis* SFA-H31 and includes an optimized method for producing of acetoin using this strain. The advantage of this method to produce acetoin has been defined by its high-yield without mixture with diacetyl or 2,3-butanediol, both of which are usually accompanied with acetoin in other strain. This *Bacillus subtilis* mutant strain has been deposited in China General Microbiological Culture Collection (CGMCC) and the accession number is CGMCC No. 1869, in which the process of fermentation for acetoin production is composed of (1) strain activation, (2) seed culture, (3) fermentation, (4) quantification of substrates and products. Based on current method, the concentration of acetoin in the ferment broth can reach to 35-55 g/L and the conversion rate of glucose to acetoin is in the range of 40-50%.

2 Claims, 3 Drawing Sheets

BACILLUS SUBTILIS MUTANT STRAIN AND A FERMENTATION METHOD FOR PRODUCING ACETOIN USING THIS ORGANISM

CROSS-REFERENCE TO RELATED APPLICATIONS

This application claims priority to Chinese Patent Applications No. 200710013403.X filed on Jan. 29, 2007, and 200710013402.5 filed on Jan. 29, 2007, the contents of which are incorporated herein by references.

BACKGROUND OF THE INVENTION

1. Field of the Invention

The present invention relates to a mutant strain of *Bacillus subtilis* and its application in preparing acetoin, especially relates to a mutant strain of *Bacillus subtilis* CGMCC No. 1869 and its application in producing acetoin of high purity.

2. Description of the Related Art

Acetoin (acetylmethylcarbinol) widely exists in corn, grape, apple, banana, cheese, meat and many other foods. Acetoin contributes the special butter flavor to all these foods. And beer flavor is also related to acetoin.

Acetoin is a broadly used as one of the food flavors in the world, and it is also an important chemical compound and a medicine intermediate. Acetoin can be used to synthesize diacetyl and 2,3-butanediol. As a chiral compound, it can be used to synthesize some rare medicines and medical intermediates, such as 4-chloro-4,5-dimethyl-1,3-dioxolan-2-one (CDMDO), an important intermediate mainly used for modifying penicillin, ampicillin and other antibiotics to increase their activities and decrease their medicine side effects. In addition, acetoin can also be used to synthesize lenampicillium hydrochloride (X. H. Xiao, 2004), a precursor of half synthetic penicillin and ampicillin. Lenampicillium hydrochloride is stable in intestines and stomach, of better absorption, less bad effects and low toxicity.

Acetoin can be synthesized chemically by partial hydrogenated reduction of diacetyl (2,3-butanedione) or selective oxidization by 2,3-butanediol with the transformation efficiency of 50-80%. Acetoin can also be prepared by electron-oxidizing 2,3-butanediol with better selectivity and high yield (A. Hilmi, et al, 1997). Besides, acetoin can be produced by enzymatic conversion. For examples, an U.S. Pat. No. 5,164,314 disclosed a process for the enzymatic preparation of acetoin, which employed a diacetyl reductase from a yeast or *Lactobacillus* strain (Hummel in 1992); Susan Budavari reported that sorbose bacterium could transform 2,3-butanediol to acetoin with high yield without by-products; however, it is very complicated for addressing those specific enzymes involved in this process.

Acetoin is an important metabolite in some microorganisms, so that it also can be produced by microbial fermentation by consuming glucose. However, most reports relevant to acetoin fermentation were about the metabolic pathways and only a few of reports were related to acetoin production as a by-product of butanedione or 2,3-butanediol. In U.S. Pat. No. 5,075,226, a method was disclosed for production of diacetyl and acetoin using lactic acid bacterium by fermentation. Hespell reported that *Bacillus polymyxa* was able to utilize xylan to produce butanedione and acetoin and the maximal total yield reached to 11.3 g/L. Braneni & Keenan found diacetyl and acetion can be produced by fermentation using lactic acid bacteria, which also produced 2,3-butanediol simultaneously. Teixeira reported that *Hanseniaspora guillermondii* could produce acetoin with a yield as high as to 0.36 g/L. In present invention the inventors provide a *Bacillus subtilis* mutant strain which can produce acetoin with advantages far beyond all above.

SUMMARY OF THE INVENTION

One of two objects of the present invention is to provide a mutant strain of *Bacillus subtilis* which can produce acetoin with high yield and purity. The other one is to provide a technical procedure for producing acetoin by fermentation using this *Bacillus subtilis* mutant strain.

The *Bacillus subtilis* mutant strain described in the present invention can efficiently transform glucose to acetoin without contamination with diacetyl and 2,3-butanediol, which are usually produced together with acetoin in other strains. Therefore, the mutant strain is an ideal microorganism for the commercial-scale production of acetoin.

The strain of *Bacillus subtilis* with high potential for producing acetoin described in the present invention is a *Bacillus subtilis* mutant strain SFA-H31, which was deposited in China General Microbiological Culture Collection (CGMCC) on Nov. 23, 2006 with the accession number CGMCC No. 1869.

The morphological characteristics of the strain CGMCC No. 1869 are Gram-positive, oval endspore, without parasporal crystals, rod-shape with single or chain arrangement at the beginning, sporulation at 16-18 hours when cultured in solution at 37° C. (see FIG. 1 and FIG. 2 for shapes and spores), flat colony (round at the beginning and irregular gradually with smooth and dull surface later). The physiological and biochemical characteristics of the bacterium are aerobic, chemoheterotrophic, acid production from glucose, fructose, mannose, maltose, sucrose and trehalose, no glucose ferment, no citrate utilization, catalase positive, with the ability to reduce nitrate. All above characteristics of the strain CGMCC NO. 1869 are summarized in table 1. Comparing to *Bacillus subtilis* model strain, CGMCC NO. 1869 fails to utilize citrate, which might be one of the effectors of gene mutations.

TABLE 1

Comparison of the strain CGMCC NO. 1869 with standard *Bacillus subtilis*

| Property | B. subtilis* | CGMCC NO. 1869 |
| --- | --- | --- |
| Diameter of cell > 1.0 um | − | − |
| round spore | − | − |
| Spore sac expand | − | − |
| Parasporal crystals | − | − |
| Anaerobic growth | − | − |
| V-P test | + | + |
| Acid production from: | | |
| D-Glucose | + | + |
| Arabinose | + | + |
| D-xylose | + | + |
| D-mannose | + | + |
| Fermentation of Glucose | − | − |
| Hydrolysis of: | | |
| Casein | + | + |
| Gelatin | + | + |
| Starch | + | + |
| Tyrosine | − | − |
| Utilization of: | | |
| Citrate | + | − |
| Propionate | − | − |
| Catalase | + | + |
| Phenylalanine Dehydrogenase | − | − |

TABLE 1-continued

Comparison of the strain CGMCC NO. 1869 with standard *Bacillus subtilis*

| Property | B. subtilis* | CGMCC NO. 1869 |
|---|---|---|
| Alkaline phosphatase | − | − |
| Reduction of Nitrate | + | + |
| Production of indole | − | − |
| Needed: | | |
| NaCl, KCl | − | − |
| Urate | − | − |
| Growing pH: | | |
| nutrient broth 6.8 | + | + |
| 5.7 nutrient broth | + | + |
| Growth NaCl: | | |
| 2% | + | + |
| 5% | + | + |
| 7% | + | + |
| 10% | ND | − |
| Growth Temp. ° C.: | | |
| 5 | − | − |
| 10 | + | + |
| 30 | + | + |
| 40 | + | + |
| 50 | ND | + |
| 55 | − | − |
| 65 | − | − |

+, positive;
−, negative;
ND, not definite
*See reference: Dong Xiuzhu, Cai Miaoying etc, Manual of Systematic Determinative Bacteriology, Science Pub(P. R. China). 2001, p. 62-63

The sequence of 16S rDNA of strain CGMCC NO. 1869 of the present invention contains 1,468 base pairs (see SEQ ID NO. 1), and was submitted to NCBI GenBank with an accession number: EF159949.

Comparing the sequences of the 16S rRNA gene of CGMCC NO1869 with known 16S rRNA genes from several *Bacillus subtilis* stains, such as *Bacillus subtilis* CICC10073 ((GenBank accession no. AY881645), *Bacillus subtilis* Y7-1 ((GenBank accession no. AB300816), *Bacillus subtilis* CICC10147((GenBank accession no. AY971364))(see FIG. 3), it reveals 100% similarity between each other, demonstrating the strain of CGMCC NO. 1869 belongs to *Bacillus subtilis*.

The identities of 16S rRNA gene sequences and applications of different *Bacillus subtilis* strains including CGMCC No. 1869, CICC10147 and CICC10073 are listed in Table 2. Both CICC10147, CICC10073 were deposited in China center of Industrial Culture Collection CICC, and they can produce thermophilic amylase and protease, respectively. The different applications indicate their specificities.

TABLE 2

Similarity comparison of 16S rDNA and application of CGMCC NO. 1869 and two other *Bacillus subtilis* strains

| Strain | Length of 16S rDNA (bp) | Similarity | Usage |
|---|---|---|---|
| CGMCC NO. 1869 | 1468 | | Producing Acetoin |
| CICC10147 | 1498 | 2-1468 bp 100% | Producing thermophilic amylase |
| CICC10073 | 1487 | 2-1468 bp 100% | Producing protease |

The solid medium above-described for morphological observation is composed of (g/L): glucose 5, peptone 5, yeast extract 5, sodium chloride 3, magnesium sulfate m.0.1, agar 20, and pH7.0-7.2.

The liquid medium above-described for morphological observation is composed of (g/L): glucose 5, peptone 5, yeast extract 5, sodium chloride 3, magnesium sulfate 0.1, pH7.0-7.2.

For the experimental method above-described for characterizing the bacterial morphological and biochemical properties please refer to Dong Xiuzhu, Cai Miaoying etc, "Manual of Systematic Determinative Bacteriology, Science Pub. 2001, p 364-398".

In the present invention, the steps to produce acetoin from *B. subtilis* CGMCC NO1869 are listed as follows:

(1) Microorganism: *Bacillus subtilis* CGMCC NO. 1869 provided in the present invention.

(2) Strain activation: a loop of the organism is inoculated to the slant and incubated in an incubator at 35-40° C. for 24-48 hours for ready.

(3) Liquid seed culture: one or two loops of the cultivation in step (2) are inoculated to 30-40 ml of liquid seed medium (250 ml flask), and incubated on a shaker at 150-180 rpm for 12-18 hours at 35-40° C.

(4) Fermentation: Shaking

Flask fermentation: the culture product in step (3) inoculates in a 500 ml flask supplied with 80-100 ml fermentation medium with 1-5% (v/v) ratio and then incubated at 35-40° C., 150-180 rpm for 48-72 hours. When glucose in the medium is exhausted, the fermentation process should be terminated. 50 L-fermentor fermentation: the culture product in step (3) is inoculated in the fermentor (50 L) supplied with 30-35 L of the fermentation medium with 1-5% (v/v) ratio. Then the inoculated medium is incubated at 35-40° C. for 40-70 hours. During incubation, the dissolved oxygen concentrations should be maintained at 5-20% by adjusting the rotation speed and aeration ratio, and the pH of the medium should be 7.0 to 7.5 at the time of inoculation and kept at 6.0 to 7.0 by adding with 20% sodium hydroxide or 20% sulphuric acid aqueous solution during cultivation. The concentrations of glucose and acetoin in broth should be measured at different time points, and the fermentation should be terminated when they become stable.

(5) Quantification of substrates and products: the concentrations of glucose and acetoin in the supernatant of fermentation broth are measured. The supernatants can be collected by centrifuging the broth at 3000-3500 rpm for 5-8 min. Based on the measurement, the production yield of acetoin from glucose can be calculated. Meanwhile, the fermentation broth is collected and vacuumed or atmospheric distilled at 80 to 100° C., and the gas chromatograph is performed to analyze the purity of acetoin The slant medium above-described is composed of (g/L): glucose 5 g, peptone 5 g, yeast extract 5 g, sodium chloride 3 g, magnesium sulfate 0.1 g, agar 20 g, pH7.0-7.2 dissolve in deionized water.

The seed medium above-described is composed of (g/L) glucose 20-25 g, yeast extract 2 g. dihydropotassium phosphate 0.1 g, dipotassium hydrogen phosphate 0.1 g, pH7.0-7.2 dissolve in tap-water.

The fermentation medium above-described is composed of (g/L) glucose 80-140 g, yeast extract 2 g, corn steep liquor 10 g, pH7.0-7.2 dissolve in tap-water.

In the process for preparing acetoin above-described, optimum culture temperature in step (2) (3) (4) is 37° C.±0.2° C.

In the process for preparing acetoin above-described, the optimum culture time in step (2) is 30 hours.

In the process for preparing acetoin above-described, the optimum culture time in step (3) is 12-14 hours.

In the process for preparing acetoin above-described, the optimum glucose concentration in the fermentation medium in step (4) is 100 g/L-120 g/L.

In the process for preparing acetoin above-described, the optimum dissolved oxygen concentration in step (4) is 10%-15%.

In the process for preparing acetoin above-described, the optimum pH in the broth in step (4) is 6.5±0.2.

The glucose concentrations of the broth above-described are measured by a biosensor with glucose dehydrogenase electrode (Institute of Biology, Shandong Academy of Sciences, SBA-40C)

The acetoin concentrations of the broth above-described are measured by a colorimetric method referring to W. W. Westerfeld, A colorimetric determination of blood acetoin. J. Biol. Chem., 1945; 161: 495-502.

The purity of acetoin is analyzed by a GC system (GC9790, Fuli Analytical Instrument Co., LTD, China) equipped with a flame ionization detector and a GEP-20M capillary column. The operation conditions are as follows: nitrogen was used as the carrier gas, the injector temperature and the detector temperature were both 200° C., and the column oven is kept constant at 100° C. for 3 min and then programmed to 180° C. with a temperature increase of 8° C. $min^{-1}$ and at 180° C. kept for 3 min with 1 µl of injection and 5:1 split ratio. The peaks of acetion, diacetyl and 2,3-butanediol are at 8.7 min, 4.5 min and 13.5 min around respectively.

The *Bacillus subtilis* CGMCC NO1869 of the present invention can transform glucose to acetoin with high yield and high purity. It is also stable for producing highly acetoin without producing diacetyl or 2,3-butanediol both joint compounds with acetoin in some other microorganisms and it is a potential strain for commercial-scale production of acetoin.

The *Bacillus subtilis* CGMCC NO1869 of the present invention can efficiently transform glucose to acetoin with high yield and without contamination with diacetyl and 2,3-butanediol, which are usually produced accompanied with acetoin in other strains. Therefore, it is a potential strain for the commercial-scale production of acetoin.

The maximal yield of acetoin of *Bacillus subtilis* CGMCC NO. 1869 can reach to over 55 g/L utilizing glucose as raw material and the average acetoin yield on glucose is over 45%, the highest is up to 50%. The distillate of the broth is used to analyze the purity of acetoin by gas chromatograph, the average peak area of acetoin is 95% of the total area, and the highest is over 98%.

BRIEF DESCRIPTION OF THE DRAWINGS

The *Bacillus subtilis* mutant strain SFA-H3 has been stored in China General Microbiological Culture Collection (CGMCC) on Nov. 23, 2006, and the address is Datun Road, Chaoyang District, Beijing 100101, P. R. China, the accession number is CGMCC No. 1869.

DETAILED DESCRIPTION OF THE INVENTION

The present invention can be explained more specifically by following examples.

EXAMPLES

Example 1

16S rDNA Sequencing of CGMCC NO1869

The present invention entrusts TaKaRa Biotechnology (Dalian) Co., Ltd. to sequence the 16S rDNA of the strain CGMCC NO1869. The process is as follows: a loop of slant culture is put in 10 µl sterile water, after denatured at 99° C., centrifuged and the supernatant is taken as the template, the TaKaRa 16S rDNA Bacterial Identification PCR Kit (Code No. D310) Forward/Reverse primer2 as primer, PCR the 16rDNA of the strain CGMCC NO1869. 5 µl is used for electrophoresis. Recovery the aim fragment using TaKaRa Agarose Gel DNA Purification Kit Ver.2.0 (Code No. DV805A). Seq Forward, Seq Reverse Seq Internal is used as primer to sequence the aim fragment.

The result: the length of 16S rDNA of the *Bacillus subtilis* strain CGMCC NO1869 is 1468 bp (refer to SEQ ID NO. 1).

Figure 1:
FIG. 1 is the cell shape of the strain CGMCC NO1869 (×1600)
Figure 2:
FIG. 2 is the cell and the spore shapes of the strain CGMCC NO1869 (×1600)
Figure 3:
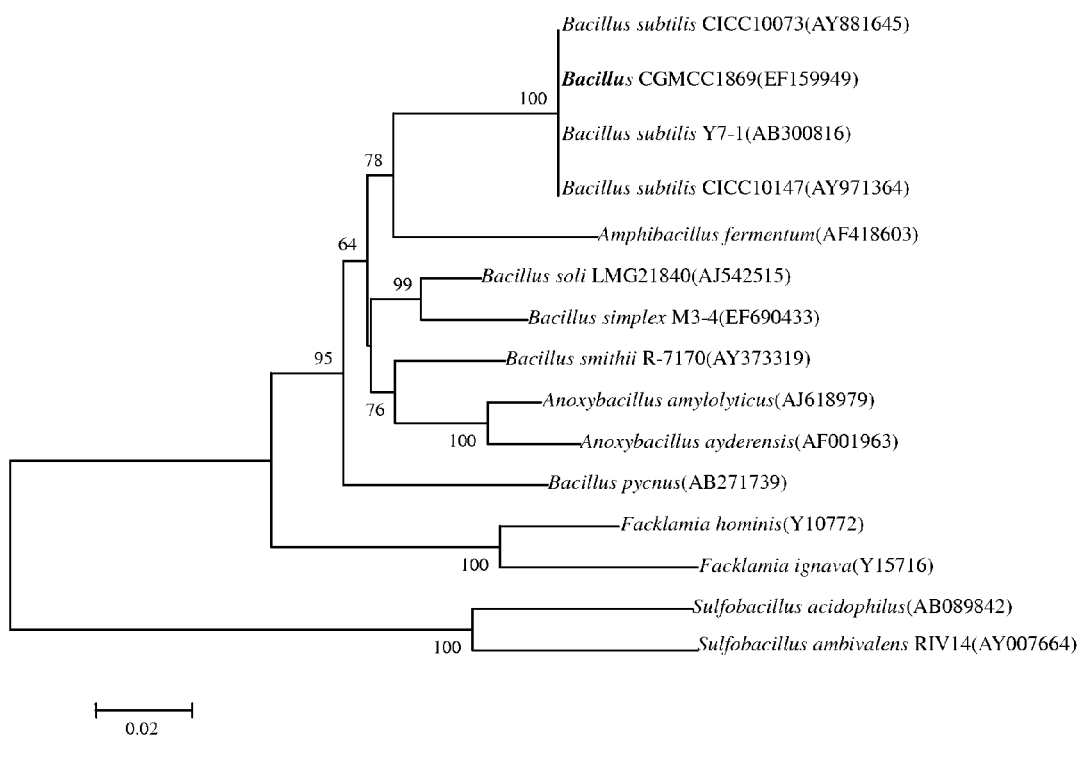
FIG. 3 is the phylogenetic tree of the strain CGMCC NO1869.

The sequence of the 16S rDNA of CGMCC NO1869 is compared with known 16S rRNA gene sequences in the NCBI GenBank database by the program BLASTN, it is found the 16S rDNA sequence of CGMCC NO1869 is highly identity to 16S rDNA of *Bacillus subtilis* registered in NCBI. It phylogenetic tree is as FIG. 3. That indicates CGMCC NO 1869 strain is a *Bacillus subtilis*.

Example 2

The process for producing of acetoin by fermentation of *Bacillus subtilis* CGMCC NO 1869 is as follows:

(1). Microorganism: CGMCC NO1869

(2). Strain activation: a loop of the organism is inoculated to a slant (composed of (g/L): glucose 5, peptone5, yeast extract 5, sodium chloride 3, magnesium sulfatem.0.1, agar 20, pH7.0-7.2) and incubated in an incubator at 37° C. for 30 hours.

(3). Liquid seed culture: two loops of the cultivation in step (2) are inoculated to 30 ml (250 ml flask) liquid seed medium (composed of (g/L): glucose 22, yeast extract 20, dihydropotassium phosphate 0.1, dipotassiumhydrogen phosphate 0.1, pH7.0-7.2), and incubated on a shaker at 160 rpm and 37° C. for 12 hours.

(4). Fermentation: the culture product in step (3) is added in 80 ml fermentation medium (composed of (g/L) glucose 110, yeast extract 2, corn steep liquor 10, pH7.0-7.2) in a 500 ml flask with 1-5% (v/v) ratio and incubated at 37° C., When glucose in medium is exhausted at 62 hours, the fermentation process is stopped.

(5) Quantification of acetoin: the fermentation broth is centrifuged at 3000 rpm for 8 min., acetoin in the supernatant is then measured, and then calculate the acetoin yield on glucose. At same time, the fermentation broth is collected and vacuumed distilled at 80° C., the purity of acetoin is analyzed by gas chromatography. The acetoin concentration in broth is 47.5 g/L, the acetoin yield on glucose is 43.2% and the peak area of acetoin takes 94.7% of the total area.

Example 3

Figure 4:
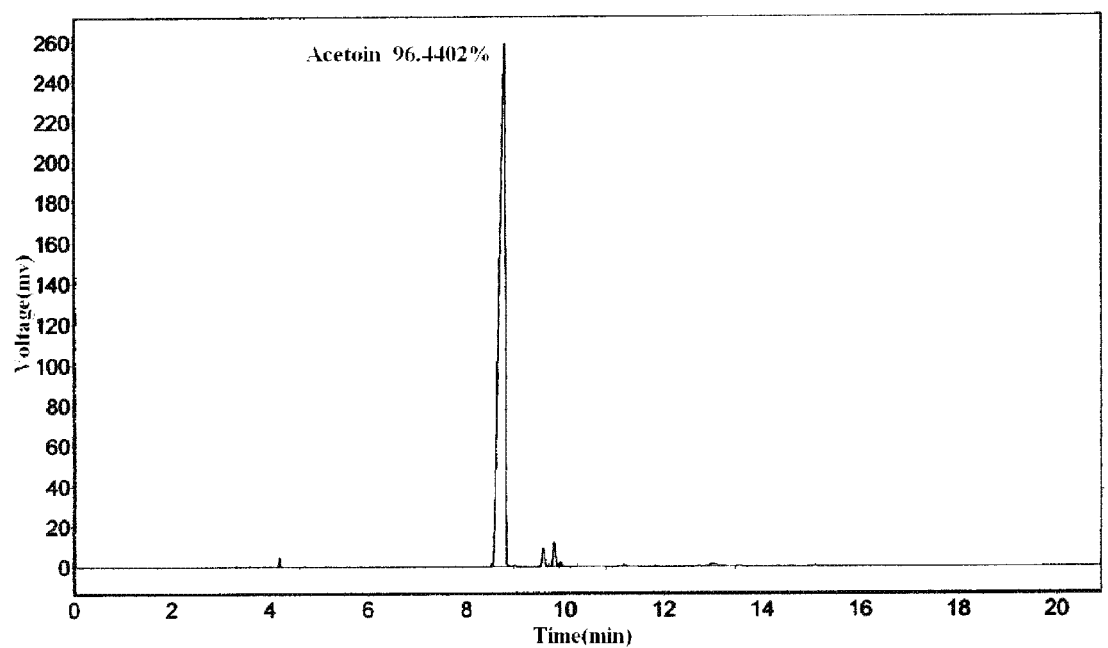
FIG. 4 is the gas chromatogram of the distillate of the CGMCC NO1869 fermentation broth, the peak of acetion is at 8.768 min. This area takes 96.4% of the total area.

The process for producing of acetoin by fermentation of *Bacillus subtilis* CGMCC NO 1869 is as follows:
(1). Microorganism: CGMCC NO1869
(2). Strain activation: a loop of the organism is inoculated to a slant (composed of (g/L): glucose 5, peptone5, yeast extract 5, sodium chloride 3, magnesium sulfatem.0.1, agar 20, pH7.0-7.2) and incubated in an incubator at 37° C. for 40 hours.
(3). Liquid seed culture: two loops of the cultivation in step (2) are inoculated to 60 ml (500 ml flask) of liquid seed medium (composed of (g/L) glucose 22 g, yeast extract 20 g, dihydropotassium phosphate 0.1 g, dipotassiumhydrogen phosphate 0.1 g, pH7.0-7.2), and incubated on a shaker at 150 rpm and 37° C. for 14 hours.
(4). Fermentation: 4% (v/v) culture in step (3) is inoculated in a 50 L fermentor supplied with 33 L of the culture medium, which composed of (g/L) glucose 115, yeast extract 2, corn steep liquor 10, pH7.0-7.2, and then incubated at 37° C. During incubation, the dissolved oxygen concentration is maintained at 10-15% by adjusting the rotation speed and aeration ratio, the pH of the medium is kept at 6.5 by adjusting with 20% sodium hydroxide or 20% sulphuric acid aqueous solution during cultivation. When glucose in the medium is exhausted at 52 hours, the fermentation process is stopped.
(5) Quantification of acetoin: the fermentation broth is centrifuged at 3000 rpm for 8 min, acetoin in the supernatant is then measured, and then calculate the acetoin yield on glucose. At the same time, the fermentation broth is collected and vacuumed distilled at 80° C., the purity of acetoin is analyzed by gas chromatography. The acetoin concentration in broth is 52.5 g/L, the acetoin yield on glucose is 45.7% and the peak area of acetoin takes 96.4% of the total area (see FIG. 4).

Example 4

The process for producing of acetoin by CGMCC NO 1869 is as follows:
(1). Microorganism: CGMCC NO1869
(2). Strain activation: a loop of the organism is inoculated to a slant (composed of (g/L) glucose 5, peptone5, yeast extract 5, sodium chloride 3, magnesium sulfatem.0.1, agar 20, and pH7.0-7.2) and incubated in an incubator at 35° C. for 40 hours.
(3). Liquid seed culture: two loops of the cultivation in step (2) are inoculated to 60 ml (500 ml flask, repeating 10 flasks) liquid seed medium (composed of (g/L)glucose 20, yeast extract 2, dihydropotassium phosphate0.1, dipotassium hydrogen phosphate 0.1, pH7.0-7.2) and incubated on a shaker at 150 rpm and 35° C. for 14 hours.
(4). Fermentation: 4% (v/v) culture in step (3) is inoculated in 50 L fermentor supplied with 33 L of the culture medium (composed of (g/L): glucose 80, yeast extract 2, corn steep liquor 10, pH7.0-7.2) and then incubated at 37° C. During incubation, the dissolved oxygen concentration is maintained at 10-15% by adjusting the rotation speed and aeration ratio, the pH of the medium is kept at 6.5 by adjusting with 20% sodium hydroxide or 20% sulphuric acid aqueous solution during cultivation. When glucose in the medium is exhausted at 48 hours, the fermentation process is stopped.
(5) Quantification of acetoin: the fermentation broth is centrifuged at 3200 rpm for 6 min., acetoin concentrations in supernatant is measured, and then calculate the acetoin yield on glucose. At same time, the fermentation broth is collected and vacuumed distilled at 90° C., the purity of acetoin is analyzed by gas chromatography. The acetoin concentration in broth is 35.5 g/L, the acetoin yield on glucose is 44.5% and the peak area of acetoin takes 96.8% of the total area.

Example 5

The process for producing acetoin is as follows:
(1). Microorganism: CGMCC NO1869
(2). Strain activation: a loop of the organism is inoculated to a slant and incubated in an incubator at 40° C. for 24 hours.
(3). Liquid seed culture: a loop of the cultivation in step (2) is inoculated to 40 ml (250 ml flask) liquid seed medium (composed of (g/L)glucose 20, yeast extract 2, dihydropotassium phosphate 0.1, dipotassium hydrogen phosphate 0.1, pH7.0-7.2) and incubated on a shaker at 180 rpm and 37° C. for 12 hours. Then 2% of this culture is inoculated to 100 ml (500 ml flask, repeating 18 flasks) liquid seed medium and cultivated at 40° C. for 20 hours as the second grade liquid seed continuously.
(4). Fermentation: the culture product in step (3) is inoculated in a 50 L fermentor with 35 L of fermentation medium with 5% (v/v) ratio. Then the inoculated medium is incubated at 38° C. During incubation, the dissolved oxygen concentration is maintained at about 20% by adjusting the rotation speed and aeration ratio, and the pH of the medium should be kept at 7.4-7.5 by adjusting with 20% sodium hydroxide or 20% sulphuric acid aqueous solution. The initial concentration of glucose in the medium is 122 g/L, and at 68 hours the glucose in the medium is exhausted.
(5) Quantification of acetoin: the fermentation broth is centrifuged at 3200 rpm for 6 min., acetoin concentration in the supernatant is measured, and then calculate the acetoin yield on glucose. At same time, the fermentation broth is collected and vacuumed distilled at 90° C., the purity of acetoin is analyzed by gas chromatography. The concentration of acetoin in broth is 53.5 g/L, the acetoin yield on glucose is 43.8% and the peak area of acetoin takes 95.8% of the total area.

Example 6

The process for producing of acetoin is as follows:
(1). Microorganism: CGMCC NO1869
(2). Strain activation: a loop of the organism is inoculated to a slant and incubated in an incubator at 40° C. for 24 hours.
(3). Liquid seed culture: two loops of the cultivation in step (2) are inoculated to 40 ml (250 ml flask) liquid seed medium shaken at 180 rpm and 37° C. for 12 hours, and then 2% this culture is inoculated to 100 ml (500 ml flask, repeating 18 flasks) of liquid seed medium and incubated on a shaker at 180 rpm and 40° C. for 20 hours as the second grade liquid seed continuously.
(4). Fermentation: 5% (v/v) inoculum culture in step (3) is inoculated to a 50 L fermentor supplied with 35 L of the culture medium (the initial concentration of glucose is 122 g/L) and then incubated at 36° C. During incubation, the dissolved oxygen concentration is maintained at 5-20% by adjusting the rotation speed and aeration ratio, and the pH of the medium is kept at 6.0-7.0 by adjusting with 20% sodium hydroxide or 20% sulphuric acid aqueous solution. At 64 hours glucose in the medium is exhausted and the fermentation process is stopped after 4 hours.
(5) Quantification of acetoin: the fermentation broth is centrifuged at 3200 rpm for 6 min., acetoin concentrations in the supernatant is measured, and then calculate the acetoin yield on glucose. At same time, the fermentation broth is collected and vacuumed distilled at 90° C., the purity of acetoin is analyzed by gas chromatography. The acetoin concentration in broth is 55.5 g/L, the acetoin yield on glucose is 47.0% and the peak area of acetoin takes 97.8% of the total area.

Example 7

The *Bacillus subtilis* strain CGMCC NO1869 is inoculated and activated on slant at 36° C. for 40 hours for ready.

The liquid seed is prepared by growing the organism in 30 ml seed medium (composed of (g/L): glucose 25, yeast extract 2, dihydropotassium phosphate 0.1, dipotassium hydrogen phosphate 0.1, pH7.0-7.2, are autoclaved at 118° C. for 25 min) in a 250 ml flask by being shaken at 150 rpm and 37° C. for 12 hours. The cells density, measured by the absorption at 610 mn, is 0.358 (to dilute in 10 times).

3 ml above seed cultures is inoculated in a 500 ml flask containing 80 ml culture medium (the initial concentration of glucose is 115 g/L) and then incubated with shaking at 37° C. and 150 rpm for 68 hours. Then the fermentation broth is centrifuged at 3000 rpm for 5 min, glucose and acetoin in the supernatant are OWL and 53.5 g/L separately, the acetoin production yield on glucose is 46.52%.

The purity of acetoin of the broth is analyzed by gas chromatograph with the method above-described; the peak area of acetoin takes 94.3% of the total area.

Example 8

The *Bacillus subtilis* strain CGMCC NO1869 is inoculated and activated on slant at 37° C. for 38 hours for ready.

The liquid seed culture is prepared by growing the organism in 100 ml seed medium (with the initial glucose concentration of 20 g/L, yeast extract 2, dihydropotassium phosphate 0.1, dipotassium hydrogen phosphate 0.1, and pH7.0-7.2, autoclaved at 118° C. for 25 min) in a 500 ml flask by being shaken a at 37° C. and 180 rpm for 14 hours, the optical density of the broth at 610 mn is 0.326 (to dilute in 10 times).

600 ml above seed cultures is inoculated in a 50 L fermentor supplied with 30 L fermentation medium (the glucose concentration is 116.4 g/L) and then incubated at 37° C., adjusting rotation speed and aeration ratio to maintain the dissolved oxygen concentrations at about 5-10%, the pH is kept at 6.5±0.2 by adding 20% sodium hydroxide or 20% sulphuric acid aqueous solution during cultivation. At 58 hours glucose in the medium is exhausted and the fermentation process is stopped. The fermentation broth is centrifuged at 3500 rpm for 5 min. the concentrations of glucose and acetoin in the supernatant are 0 g/L and 54.5 g/L separately, the acetoin production yield on glucose is 46.8%.

The distillate of the broth is analyzed by gas chromatograph with the method above-described; the peak area of acetoin takes 96.3% of the total area.

Example 9

The *Bacillus subtilis* strain CGMCC NO1869 is inoculated and activated on slant at 37° C. for 38 hours for using.

The liquid seed culture is prepared by growing the organism in 100 ml seed medium with the initial glucose concentration of 20 g/L, yeast extract 2, dihydropotassium phosphate 0.1, dipotassium hydrogen phosphate 0.1, pH7.0-7.2, autoclaved at 118° C. for 25 min in a 500 ml flask by being shaken at 37° C. and 180 rpm for 14 hours, the optical density of the broth at 610 mn is 0.326 (to dilute by 10 times).

800 ml above seed cultures is inoculated in a 50 L fermentor supplied with 32 L fermentation medium (the glucose concentration is 108.4 g/L) and then incubated at 37° C., adjusting rotation speed and aeration ratio to mantain the dissolved oxygen concentrations at about 5-10%, the pH is kept at 6.0-6.5 by adding 20% sodium hydroxide or 20% sulphuric acid aqueous solution during cultivation. At 52 hours glucose in the medium is exhausted and the fermentation process is stopped after 4 hours. The concentrations of glucose and acetoin in the supernatant are 0 g/L and 54.0 g/L separately, and the acetoin production yield on glucose is 49.8%.

The purity of acetoin of the broth is analyzed by gas chromatograph; the peak area of acetoin takes 98.3% of the total area.

Example 10

The *Bacillus subtilis* strain CGMCC NO1869 is inoculated and activated on slant at 37° C. for 38 hours for using.

The liquid seed culture is prepared by growing the organism in 100 ml seed medium (with glucose 20 g/L, yeast extract 2 g/L, dihydropotassium phosphate 0.1 g/L, dipotassium hydrogen phosphate 0.1 g/L, pH7.0-7.2, autoclaved at 118° C. for 25 min) in a 500 ml flask by being shaken at 37° C. and 180 rpm for 14 hours, the optical density of the broth at 610 mn is 0.326 (to dilute in 10 times).

500 ml above seed cultures inoculates in a 50 L fermentor supplied with 35 L fermentation medium (the initial concentration of glucose is 136.4 g/L) and then incubated at 37° C., adjusting rotation speed and aeration ratio to mentain the dissolved oxygen concentrations at about 10-15%, the pH is kept at 6.2±0.2 by adding 20% sodium hydroxide or 20% sulphuric acid aqueous solution during cultivation. At 78 hours the concentrations of glucose and become stable, so the fermentation process is stopped. The concentrations of glucose and acetoin in the supernatant are 15 g/L and 54.5 g/L separately, the acetoin production yield on glucose is 44.9%.

The purity of acetoin is analyzed by gas chromatograph; the peak area of acetoin takes 93.5% of the total area.

In the example, glucose is measured by a biosensor with glucose dehydrogenase electrode (Institute of Biology, Shandong Academy of Sciences, SBA-40C)

In the example, acetoin is measured by a colorimetric method, refers to W. W. Westerfeld, A colorimetric determination of blood acetoin. J. Biol. Chem., 1945; 161: 495-502). The steps are listed as follows:

Standard curve is created according to the order in the table below, varies of reagents and solutions are added in each tube and then kept at 60° C. for coloration for 15 min., absorbance is evaluated at 530 nm.

|  | Tube No | | | | | | | |
| --- | --- | --- | --- | --- | --- | --- | --- | --- |
| Item | 1 | 2 | 3 | 4 | 5 | 6 | 7 | 8 |
| Acetoin standard solution (ml) | 0 | 0.20 | 0.40 | 0.60 | 0.80 | 1.00 | 1.20 | 1.40 |
| Acetoin (µg) | 0 | 2 | 4 | 6 | 8 | 10 | 12 | 14 |
| Distilled water (ml) | 6 | 5.8 | 5.6 | 5.4 | 5.2 | 5.0 | 4.8 | 4.6 |
| α-naphthol (ml) | 1.0 | 1.0 | 1.0 | 1.0 | 1.0 | 1.0 | 1.0 | 1.0 |
| creatine (ml) | 1.0 | 1.0 | 1.0 | 1.0 | 1.0 | 1.0 | 1.0 | 1.0 |

In which:
Acetoin standard solution (40 ug/ml): 0.2000 g acetoin (Sigma, purity>99.0%) dissolved in 100 ml deionized water, diluted 50 times before using.
5% α-naphthol: 1 g powdered colorless α-naphthol (redistilled under nitrogen) dissolved in 20 ml. 2.5M NaOH. The solution is prepared immediately before using.

0.5% creatine: 1 g creatine dissolved in 200 ml deionized water.

The fermentation broth is centrifuged at 3500-4000 rpm for 5-8 min and then the concentration of acetoin in the supernatant is measured by the colorimetric method as above-described.

The 16SrDAN sequence of *Bacillus subtilis* CGMCC NO. 1869 is as following:

```
                                           SEQ ID NO. 1
<110> Shandong Food Ferment Industry Research
Design Institute <120> A Bacillus subtilis strain can produce
acetoin with high yield

<141> 2007-10-8

<160> 1

<210> 1

<211> 1468

<212> DNA

<213> Bacillus subtilis

<221> Bacillus subtilis CGMCC NO. 1869 16S rDNA

<222> (1) . . . (1468)

<400> 1
acgacgctgg cggcgtgcct aatacatgca agtcgagcgg        60
acagatggga gcttgctccc tgatgttagc ggcggacggg tgagtaacac gtgggtaacc       120
tgcctgtaag actgggataa ctccgggaaa ccggggctaa taccggatgg ttgtttgaac       180
cgcatggttc aaacataaaa ggtggcttcg gctaccactt acagatggac ccgcggcgca       240
ttagctagtt ggtgaggtaa cggctcacca aggcaacgat gcgtagccga cctgagaggg       300
tgatcggcca cactgggact gagacacggc ccagactcct acgggaggca gcagtaggga       360
atcttccgca atggacgaaa gtctgacgga gcaacgccgc gtgagtgatg aaggttttcg       420
gatcgtaaag ctctgttgtt agggaagaac aagtaccgtt cgaatagggc ggtaccttga       480
cggtacctaa ccagaaagcc acggctaact acgtgccagc agccgcggta atacgtaggt       540
ggcaagcgtt gtccggaatt attgggcgta aagggctcgc aggcggtttc ttaagtctga       600
tgtgaaagcc cccggctcaa ccggggaggg tcattggaaa ctggggaact tgagtgcaga       660
agaggagagt ggaattccac gtgtagcggt gaaatgcgta gagatgtgga ggaacaccag       720
tggcgaaggc gactctctgg tctgtaactg acgctgagga gcgaaagcgt ggggagcgaa       780
caggattaga taccctggta gtccacgccg taaacgatga gtgctaagtg ttaggggggtt      840
tccgcccctt agtgctgcag ctaacgcatt aagcactccg cctggggagt acggtcgcaa       900
gactgaaact caaaggaatt gacggggggcc cgcacaagcg gtggagcatg tggtttaatt      960
cgaagcaacg cgaagaacct taccaggtct tgacatcctc tgacaatcct agagatagga      1020
cgtccccttc ggggggcagag tgacaggtgg tgcatggttg tcgtcagctc gtgtcgtgag      1080
atgttgggtt aagtcccgca acgagcgcaa cccttgatct tagttgccag cattcagttg      1140
ggcactctaa ggtgactgcc ggtgacaaac cggaggaagg tggggatgac gtcaaatcat      1200
catgcccctt atgacctggg ctacacacgt gctacaatgg acagaacaaa gggcagcgaa      1260
accgcgaggt taagccaatc ccacaaatct gttctcagtt cggatcgcag tctgcaactc      1320
gactgcgtga agctggaatc gctagtaatc gcggatcagc atgccgcggt gaatacgttc      1380
ccgggccttg tacacaccgc ccgtcacacc acgagagttt gtaacacccg aagtcggtga      1440
ggtaaccttt taggagccag ccgccgaagg tgggacagat gattgggg                   1468
```

SEQUENCE LISTING

```
<160> NUMBER OF SEQ ID NOS: 1

<210> SEQ ID NO 1
<211> LENGTH: 1468
<212> TYPE: DNA
<213> ORGANISM: Bacillus subtilis

<400> SEQUENCE: 1
acgacgctgg cggcgtgcct aatacatgca agtcgagcgg acagatggga gcttgctccc     60
tgatgttagc ggcggacggg tgagtaacac gtgggtaacc tgcctgtaag actgggataa    120
ctccgggaaa ccggggctaa taccggatgg ttgtttgaac cgcatggttc aaacataaaa    180
ggtggcttcg gctaccactt acagatggac ccgcggcgca ttagctagtt ggtgaggtaa    240
cggctcacca aggcaacgat gcgtagccga cctgagaggg tgatcggcca cactgggact    300
```

-continued

```
gagacacggc ccagactcct acgggaggca gcagtaggga atcttccgca atggacgaaa    360
gtctgacgga gcaacgccgc gtgagtgatg aaggttttcg gatcgtaaag ctctgttgtt    420
agggaagaac aagtaccgtt cgaatagggc ggtaccttga cggtacctaa ccagaaagcc    480
acggctaact acgtgccagc agccgcggta atacgtaggt ggcaagcgtt gtccggaatt    540
attgggcgta aagggctcgc aggcggtttc ttaagtctga tgtgaaagcc cccggctcaa    600
ccggggaggg tcattggaaa ctggggaact tgagtgcaga agaggagagt ggaattccac    660
gtgtagcggt gaaatgcgta gagatgtgga ggaacaccag tggcgaaggc gactctctgg    720
tctgtaactg acgctgagga gcgaaagcgt ggggagcgaa caggattaga taccctggta    780
gtccacgccg taaacgatga gtgctaagtg ttaggggggtt tccgccccctt agtgctgcag    840
ctaacgcatt aagcactccg cctggggagt acggtcgcaa gactgaaact caaaggaatt    900
gacgggggcc cgcacaagcg gtggagcatg tggtttaatt cgaagcaacg cgaagaacct    960
taccaggtct tgacatcctc tgacaatcct agagatagga cgtccccttc ggggcagag    1020
tgacaggtgg tgcatggttg tcgtcagctc gtgtcgtgag atgttgggtt aagtcccgca   1080
acgagcgcaa cccttgatct tagttgccag cattcagttg ggcactctaa ggtgactgcc   1140
ggtgacaaac cggaggaagg tggggatgac gtcaaatcat catgccccctt atgacctggg  1200
ctacacacgt gctacaatgg acagaacaaa gggcagcgaa accgcgaggt taagccaatc   1260
ccacaaatct gttctcagtt cggatcgcag tctgcaactc gactgcgtga agctggaatc   1320
gctagtaatc gcggatcagc atgccgcggt gaatacgttc ccgggccttg tacacaccgc   1380
ccgtcacacc acgagagttt gtaacacccg aagtcggtga ggtaaccttt taggagccag   1440
ccgccgaagg tgggacagat gattgggg                                      1468
```

What is claimed is:

1. A biologically pure culture of *Bacillus subtilis* strain SFA-H31, wherein said strain has been deposited with the CGMCC and assigned accession number CGMCC No. 1869, and said strain has the 16S rDNA sequence of SEQ ID No. 1.

2. The biologically pure culture of *Bacillus subtilis* strain SFA-H31 of claim 1, wherein said strain efficiently transforms glucose to acetoin without contamination with diacetyl or 2,3-butanediol.

* * * * *